US008734821B2

(12) United States Patent
Hollis et al.

(10) Patent No.: US 8,734,821 B2
(45) Date of Patent: *May 27, 2014

(54) SILICONE SURFACTANT-BASED AGRICULTURAL FORMULATIONS AND METHODS FOR THE USE THEREOF

(75) Inventors: Shannon Hollis, Delaware, OH (US); Jason Rader, Marysville, OH (US); Casey McDonald, Galloway, OH (US)

(73) Assignee: OMS Investments, Inc., Los Angeles, CA (US)

( * ) Notice: Subject to any disclaimer, the term of this patent is extended or adjusted under 35 U.S.C. 154(b) by 980 days.

This patent is subject to a terminal disclaimer.

(21) Appl. No.: 11/801,466

(22) Filed: May 10, 2007

(65) Prior Publication Data

US 2007/0266750 A1    Nov. 22, 2007

Related U.S. Application Data

(60) Provisional application No. 60/800,545, filed on May 15, 2006.

(51) Int. Cl.
*A01N 25/32* (2006.01)

(52) U.S. Cl.
USPC .......... 424/406; 424/78.37; 424/405; 514/33; 514/772.4; 523/122

(58) Field of Classification Search
USPC ................ 424/78.37; 514/772.4, 33; 523/122
See application file for complete search history.

(56) References Cited

U.S. PATENT DOCUMENTS

| | | | |
|---|---|---|---|
| 4,988,504 A | 1/1991 | Zotto et al. | |
| 5,001,248 A | 3/1991 | Grabowski | |
| 5,008,103 A | 4/1991 | Raleigh et al. | |
| 5,066,756 A | 11/1991 | Raleigh et al. | |
| 5,489,433 A | 2/1996 | Aboud | |
| 5,504,054 A * | 4/1996 | Murphy | 504/206 |
| 5,558,806 A | 9/1996 | Policello et al. | |
| 5,906,961 A | 5/1999 | Roberts et al. | |
| 5,998,331 A | 12/1999 | Policello | |
| 6,051,533 A | 4/2000 | Kajikawa et al. | |
| 6,124,301 A | 9/2000 | Aven et al. | |
| 6,221,811 B1 | 4/2001 | Policello et al. | |
| 6,327,813 B1 | 12/2001 | Ishiwatari | |
| 6,492,419 B1 | 12/2002 | Shepard | |
| 6,717,019 B2 | 4/2004 | Lassila | |
| 6,734,141 B2 | 5/2004 | Humble et al. | |
| 6,992,045 B2 | 1/2006 | Xu et al. | |
| 7,278,294 B2 | 10/2007 | Giles et al. | |
| 2003/0013683 A1 | 1/2003 | Holzer | |
| 2003/0104944 A1 | 6/2003 | Humble et al. | |
| 2005/0250805 A1 | 11/2005 | Kannan et al. | |
| 2007/0021304 A1 * | 1/2007 | Lin et al. | 504/127 |
| 2007/0037712 A1 | 2/2007 | Mosko et al. | |
| 2007/0142330 A1 | 6/2007 | Ansell | |
| 2007/0266749 A1 | 11/2007 | Rader et al. | |
| 2008/0038241 A1 | 2/2008 | Schasfoort et al. | |

FOREIGN PATENT DOCUMENTS

| | | |
|---|---|---|
| EP | 0943241 A1 | 9/1999 |
| JP | 07-206612 | 8/1995 |
| JP | 10-291903 | 4/1998 |
| JP | 11-322517 | 11/1999 |
| JP | 2003-509346 | 11/2003 |
| WO | WO 01/19190 A1 | 3/2001 |
| WO | 2007/136596 | 11/2007 |
| WO | 2007/136597 | 11/2007 |
| WO | WO 2008/110685 | 9/2008 |
| WO | WO 2009/143138 | 11/2009 |

OTHER PUBLICATIONS

Article entitled "Inert Formulations Ingredients with Activity: Toxicity of Trisiloxane Surfactant Solutions to Two-spotted Spider Mites (Acari Tetranychidae)" in Journal of Economic Entomology (Cowles et al.) vol. 93, No. 2, pp. 180-188 (2000).
Colby, S.R., "Calculating Synergistic and Antagonistic Responses of Herbicide Combinations", Maryland Agricultural Experiment Station, Contribution No. 3796, Article No. A 127, Department of Agronomy, University of Maryland, College Park, Maryland, 1978.
Felsot, A., "Formulation Basics: Inert Ingredients and Why We Need Them", Retrieved from the Internet at: www.ipmnet.org/Tim/Pesticide_Ed/Pesticide_Courses_2008/Cent_OR_Allan_Felsot_1.pdf on Jun. 30, 2009.
International Search Report and Written Opinion for International Patent Application No. PCT/US09/44495, mailed Jul. 13, 2009.
Japanese Office Action from JP 2009-510998 dated Jul. 12, 2012.
Chandler, L.D. et al., Arthropod Management Tests, 20, pp. 353-354, (1995).
Imai, T. et al., Appl. Entomol. Zool., vol. 30, pp. 380-382, Nov. 1994.
Srinivasan et al., Laboratory and Field Evaluation of Silwet L-77 and Kinetic Alone and in Combination with Imidacloprid and Abamectin for the Management of the Asian Citrus Psyllid, *Diaphorina citri* (hemiptera: psyllidae) Florida Entemologist, Mar. 2008, pp. 87-200.
Liu and Stansly, Pest Management Science, vol. 56, 861-866, (2000).
Nikolov, et al., "Superspreading Driven by Marangoni Flow", Advances in Colloid Interface Science, vol. 96, pp. 325-338, (2002).
Purcell, M.F. et al., Journal of Economic Entomology, vol. 89, pp. 1566-1570, Dec. 1996.
Shapiro, J.P. et al., Florida Entomologist, 81:, pp. 201-210, Jun. 1998.
Skinner, Arthropod Management Tests, 22, pp. 422, (1977).
Smitley and Davis, Arthropod Management Tests, vol. 22, pp. 385, (1997).
Tiiping et al., Journal of Economic Entomology, vol. 96, No. 1, 246-250 (2003).
Wood and Tedders, Hort. Science, vol. 32, pp. 1074-1076, Oct. 1997.
Woodward, "Dynamic Surface Tension and Dilational Stress Measurements Using the Drop Shape Method," pp. 1-6 (1999).
Woodward, "A Guide o FTA Video Drop Shape Software," pp. 1-4 (1999).
Woodward, "Contact Angle Measurements Using Drop Shape Method," pp. 1-8 (1999).
Zonyl Fluorosurfactants & Coating Additives, downloaded from the Internet at: http://www2.dupont.com/Zonyl_Foraperle/en_US/products/zonyl_pgs/surfactants.html, Mar. 18, 2008.

(Continued)

*Primary Examiner* — Neil Levy
(74) *Attorney, Agent, or Firm* — Hunton & Williams LLP

(57) ABSTRACT

A silicone surfactant-based synergistic agricultural formulation contains a combination of a first defined silicone surfactant and a second defined silicone surfactant in a concentration sufficient to cause a knockdown level on treated arthropods, even in the absence of known pesticidally active ingredients.

22 Claims, No Drawings

(56) References Cited

OTHER PUBLICATIONS

Siltech, LLC—Topical Report: Hydrolytic Stability Dimethicone Copolyols, © 2008.
SPI Supplies: Parafilm® M Barrier Film, downloaded from the Internet at: http://www.2spi.com/catalog/supp/supp4b.shtml Feb. 6, 2008.
The Lipid Library: Waxes—Structure, Composition, Occurrence and Analysis, downloaded from the Internet at: http://www.lipidlibrary.co.uk/Lipids/waxes/index.htm, Mar. 18, 2008.
Wikipedia: Contact Angle, downloaded from the Internet at: http://en.wikipedia.org/wiki/Contact_angle, Oct. 11, 2007.
Kruss Drop Shape Analysis System DSA100, downloaded from the Internet at: http://www.kruss.info/instruments/instruments_print/dsa100_e_print.html Nov. 6, 2007.
Yokoyama et al., "Pest Response in Packed Table Grapes to Low Temperature Storage Combined with Slow-Release Sulfur Dioxide Pads in Basic and Large-Scale Tests," J. Econ. Entomol., vol. 94, No. 4, pp. 984-988 (2001).
International Preliminary Report on Patentability for International Application No. PCT/US2009/044495, issued Dec. 2, 2010.
International Preliminary Report on Patentability for International Application No. PCT/US07/11497, completed Aug. 20, 2009.
International Preliminary Report on Patentability for International Application No. PCT/US2009/044495, issued Nov. 23, 2010.
International Search Report for International Application No. PCT/US07/11497, mailed Nov. 16, 2007.
International Search Report for International Application No. PCT/US07/11496, mailed Dec. 5, 2007.
Written Opinion for International Application No. PCT/US07/11496, mailed Dec. 5, 2007.
Written Opinion for International Application No. PCT/US07/11497, mailed Nov. 16, 2007.
Non-Final Office Action mailed Dec. 16, 2010 in co-pending U.S. Appl. No. 11/801,441.
Hollis, Co-Pending U.S. Appl. No. 12/154,105, filed May 20, 2008 (4093).
Rader, Co-Pending U.S. Appl. No. 11/801,441, filed May 10, 2007 (4097).
Supplemental European Search Report for EP 07794824.8 dated Nov. 27, 2012.
Australian Patent Examination Report No. 1 for AU Patent Application 2009249168 issued Sep. 9, 2013.

* cited by examiner

SILICONE SURFACTANT-BASED AGRICULTURAL FORMULATIONS AND METHODS FOR THE USE THEREOF

CROSS-REFERENCE TO RELATED APPLICATION

This application claims priority to Provisional Application No. 60/800,545, filed May 15, 2006, which is incorporated herein in its entirety.

BACKGROUND OF THE INVENTION

1. Field of the Invention

The present invention relates generally to agricultural formulations containing silicone surfactants and to methods for use thereof. More particularly, the formulations of the present invention contain certain combinations of silicone surfactants by which improved, synergistic agricultural efficacy is obtained.

2. Description of Related Art

Agricultural formulations can be in the form of solutions, emulsions, suspensions, dispersions and the like, and are used in agriculture for applying agricultural chemicals to plants, soil, insects and the like. Among typical agricultural chemicals are pesticides such as herbicides, insecticides, fungicides, growth regulators and the like. Other typical agricultural chemicals include plant nutrients and micronutrients.

Such agricultural formulations can contain surfactants such as trisiloxane surfactants and other silicone surfactants to enhance spreading when the formulations are applied in agriculture. However, use of silicone surfactants in agricultural formulations have been only partially effective in causing quick (less than about 60 seconds) disruption of arthropod mobility, i.e. "knockdown" (KD), even though there has been a need in the consumer market for liquid pesticidal ready-to-use products, which provide faster knockdown.

For example, known formulations often require as much as one-quarter hour or more to obtain acceptable knockdown levels against difficult to control arthropod pests, such as American cockroaches, (*Periplaneta americana*). In this regard, it should be noted that the term "arthropod" as employed herein means any invertebrate of the phylum Arthropoda including insects, spiders and other arachanids, crustaceans, and myriapods and other household pests. For purposes hereof, cockroaches are specifically to be considered to fall within the definition of arthropods.

Furthermore, although silicone surfactants have been employed extensively in herbicidal formulations as well as other applications, there has been a need in the agricultural consumer market for liquid ready-to-use products which provide enhanced efficacy when applied to substrates.

Thus, it would be advantageous to provide agricultural formulations containing silicone surfactants which provide improved knockdown rates, preferably, of about 80% or more when applied to arthropods and particularly to difficult to control arthropods such as cockroaches as well as methods for their use.

SUMMARY OF THE INVENTION

Accordingly, it is an object of the present invention to provide an agricultural product with markedly improved efficacy for treating arthropods as compared with other agricultural formulations known heretofore.

Another object of this invention is to provide agricultural products containing at least one surfactant therein for treatment of arthropods to achieve markedly improved knockdown efficacy over agricultural formulations known heretofore.

Another object is to provide stable agricultural products such as a ready-to-use consumer formulations containing certain silicone surfactant combinations that provide improved, synergistic knockdown efficacy when applied on a substrate such as the perimeter of an environment, such as a home, or on a arthropod or other substrate.

In particular, it is an object to provide compositions for treating arthropods comprising formulations having at least one silicone surfactant contained therein to cause a synergistic knockdown (KD) level when applied to arthropods.

DETAILED DESCRIPTION OF THE INVENTION

The methods and compositions of the invention are based on the use of certain combinations of silicone surfactants which provide unexpected, synergistic efficacy in agricultural applications, particularly for treatment of arthropods, and which permit use of the surfactants alone, or with an additive active ingredient.

In accordance with the present invention, a composition is provided for treating arthropods comprising a formulation containing at least one first silicone surfactant selected from the group consisting of

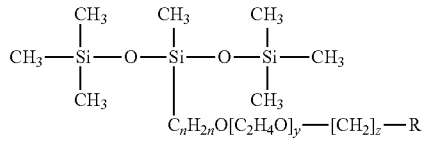

wherein: n=2-4, y=3-10, z=0-5, and R=alkyl having 1-4 carbon atoms; and at least one second silicone surfactant selected from the group consisting of

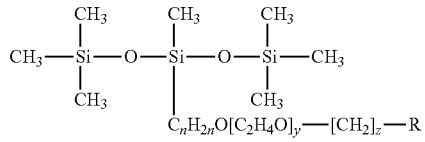

wherein: n=2-4, y=3-10, z=0-5, and R=OH or H, provided that when z=0, R=H, and when z=1-5, R=OH or O-alkyl having 1-4 carbon atoms.

Preferably, in a formulation of the present invention, the at least one first silicone surfactant and the at least one second surfactant are present in a sufficient concentration preferably, at a concentration of at least about 0.1% by weight, to cause a synergistic knockdown (KD) level on treated arthropods and, preferably, at a rate of at least about 80% within about 60 seconds after treatment of the pests with the formulation.

As a result of the synergistic knockdown levels of arthropods provided by the compositions of the present invention, unexpectedly rapid and effective control of difficult to control arthropods can be achieved.

It is further preferred that the at least one first silicone surfactant has the formula:

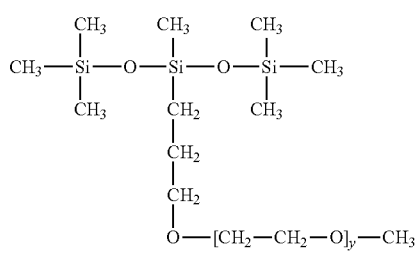

wherein y=6-10, and most preferably wherein y=8.

Exemplary of a most preferred first silicone surfactant of the above formula wherein y=8 is Silwet L-77® (General Electric Company, Waterford, N.Y.).

Similarly, it is further preferred that the at least one second silicone surfactant has the formula:

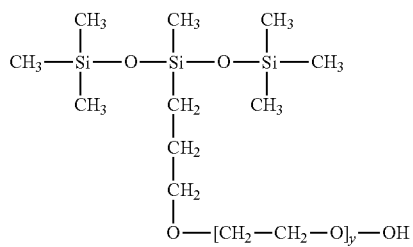

wherein y=6-10, and most preferably wherein y=8.

Exemplary of a most preferred second silicone surfactant of the above formula wherein y=8 is Silwet 408®, also known as Silwet REACH® (General Electric Company, Waterford, N.Y.).

The compositions of the present invention have been found to be unexpectedly effective in obtaining synergistic knockdown of arthropods and, particularly, difficult to knockdown arthropods, such as the American cockroach (*Periplaneta americana*), in the absence of a pesticidally active ingredient. Of course, the composition of the present invention is also effective in obtaining high and synergistic knockdown levels when agriculturally active ingredients, such as bifenthrin, for residual control, are incorporated into the composition.

The method of treating arthropods in accordance with the present invention comprises applying to an arthropod the formulation described above in a sufficient concentration to cause a synergistic knockdown level on treated arthropods, preferably, at a concentration of at least about 0.1% by weight, to cause a synergistic knockdown level, preferably, at a rate of at least 80% within about 60 seconds after treatment of the arthropods with the formulation.

To screen the efficacy of pesticides using selected surfactants and combinations of surfactants, American cockroaches, known to be difficult to knockdown, were introduced into 1.5-inch diameter polyvinyl chloride (PVC) pipe sections with stainless steel screens affixed to the bottom end. An automatic pipetter was used to apply 4.8 ml of the tested composition to each cockroach. Excess liquid was drained from the tubes through a stainless steel screen. Each cockroach was transferred to a clean polypropylene container where knockdown results were recorded at various intervals (seconds) after the application of the composition. A cockroach is determined to be knocked down when it has lost its ability to control movement about the testing container, followed by mortality. This method was also used to test various formulations containing surfactants for knockdown against house crickets (*Acheta domesticus*).

In general, an agricultural spray mixture contains water and an active agricultural chemical ingredient, such as a pesticide (including herbicides, insecticides, fungicides and growth regulators). Typically, at least 50 percent of the agricultural spray mixture is composed of water. Optionally, the agricultural spray mixture can contain at least one component selected from the group consisting of organic surfactants, antifoam agents and organic solvents. Agricultural spray mixtures are commercially available as ready-to-use products or can be prepared in a containment vessel from an agricultural chemical concentrate, water, and optionally one or more surfactants and/or antifoaming agents.

The amount of the active ingredient (i.e., agricultural chemical) in a spray mixture will be any amount effective for the intended purpose, but typically will range from about 0.001 to about 5 percent by weight based upon the total weight of the agricultural spray mixture, e.g., from about 0.03 percent to about 0.5 percent, preferably from about 0.05 percent to about 0.25 percent based upon the total weight of the agricultural spray mixture. The bulk or remainder of the agricultural spray mixture is comprised of water.

In addition, standard additives such as surfactants, solvents, biocides, antifoam agents, dispersants, antifreeze, pH modifiers, colorants, nutrients and plant growth regulators also may be included in the formulations to achieve desired results.

Illustrative pesticides which can be employed as the active ingredient in the agricultural spray mixtures of the present invention include those from the groups consisting of herbicides, insecticides, fungicides, miticides and the like.

The following specific examples are presented to further illustrate and explain certain aspects of the present invention. However, the examples are set forth for illustration only, and are not to be construed as limiting on the present invention. In the following examples, all percentages and parts are by weight unless otherwise specified.

EXAMPLE 1

The trisiloxane surfactants employed in this example are Silwet L-77® and Silwet REACH®. In the chemical structure of these surfactants, the amount of ($C_2H_4O$) represents an average. The formulations employed in this example were prepared in accordance with the following procedures:

To a first tank with an agitator, water is added, and any additional aqueous phase ingredients, are added with stirring.

In a second tank with an agitator, agriculturally active ingredients such as bifenthrin (available from FMC Corporation as Talstar MUP, a liquid concentrate containing 13.0% bifenthrin, may be incorporated into the formulation and mixed with an emulsifier.

Then trisiloxane surfactant or surfactants, Silwet L-77® and/or Silwet REACH®, is added to the second tank. The mixture is blended until homogeneous. Agitation is continued and this mixture is slowly added to the liquid in the first tank. The resulting mixture in the first tank is agitated until the final batch is totally homogeneous. At this time, other standard inert ingredients, such as solvents, biocides, pH modifiers, antifreeze, antifoam agents, colorants, nutrients, and plant growth regulators may be included in the formulation if necessary. If no agriculturally active ingredient is present, the trisiloxane surfactant or surfactants may be introduced directly into a tank with water and mixed until homogeneous.

In Table 1 below, a composition of the formulation is presented, including the indicated trisiloxane surfactant or surfactants at equal concentrations with no other active ingredient incorporated into the compositions. Components are presented in weight percent.

TABLE 1

| Surfactant Components | Formulations | | |
|---|---|---|---|
| | A | B | C |
| Silwet 408 ® (Silwet REACH) | 0.5 | 1.0 | — |
| Silwet L-77 | 0.5 | — | 1.0 |
| Water, Purified | 99.0 | 99.0 | 99.0 |
| Total % | 100.0 | 100.0 | 100.0 |

The following table presents the results of an experiment monitoring knockdown of American Cockroaches treated with the formulations prepared as noted above employing the indicated trisiloxane surfactant or surfactants at equal concentrations with no other active ingredients incorporated into the formulations.

TABLE 2

| Trisiloxane Surfactant | Formulation | Knockdown of American Cockroach 30 seconds after treatment |
|---|---|---|
| Silwet L-77 | C | 65% |
| Silwet Reach | B | 60% |
| Silwet L-77/Silwet 408 blend | A | 95% |

As illustrated by the tabulated test results, it is clear that the knockdown effect achieved by employing the Silwet L-77/Silwet REACH Blend is synergistically improved as compared with the results achieved by the individual component surfactants.

EXAMPLE 2

In Table 3 below, the compositions of the formulations, as prepared in Example 1 above, include the indicated trisiloxane surfactant or surfactants at equal concentrations with the indicated active ingredient incorporated into the compositions. Components are presented in weight percent.

TABLE 3

| Components | Formulations | | |
|---|---|---|---|
| | D | E | F |
| Talstar MUP (13% bifenthrin) | 0.39 | 0.39 | 0.39 |
| Silwet REACH | 0.50 | 1.00 | — |
| Silwet L-77 | 0.50 | — | 1.00 |
| Other inert ingredients | 1.53 | 1.53 | 1.53 |
| Water, Purified | 97.08 | 97.08 | 97.08 |
| Total % | 100.00 | 100.00 | 100.00 |

The following table presents the results of an experiment using the formulations stated in Table 3 prepared as noted above, applied to American Cockroaches:

TABLE 4

| Trisiloxane Surfactant | Formulation | Knockdown of American Cockroach 30 seconds after treatment |
|---|---|---|
| Silwet L-77 | F | 60% |
| Silwet REACH | E | 20% |
| Silwet L-77/Silwet REACH Blend | D | 85% |

Again, as illustrated by the tabulated test results, it has been demonstrated that the knockdown effect achieved employing the Silwet L-77/Silwet REACH Blend is synergistically improved as compared with the results achieved with the individual component surfactants.

EXAMPLE 3

In Table 5 below, the compositions of the formulations, as prepared in Example 1 above, include the indicated trisiloxane surfactant or surfactants with an additive active pesticidal ingredient incorporated into the formulation appropriate for substitution into S. R. Colby's Synergy Equation. Components are presented in weight percent. S. R. Colby's Synergy Equation is found in the article "Calculating Synergistic and Antagonistic Responses of Herbicide Combinations", by S. R. Colby, Apr. 11, 1966, Scientific Article No. A 1271 Maryland Agricultural Experiment Station, Department of Agronomy, University of Maryland, College Park, Md.

TABLE 5

| Components | Formulations | | |
|---|---|---|---|
| | G | H | I |
| Talstar 13% | 0.39 | 0.39 | 0.39 |
| Silwet REACH | 0.50 | 0.50 | — |
| Silwet L-77 | 0.50 | — | 0.50 |
| Other inert ingredients | 1.53 | 1.53 | 1.53 |
| Water, Purified | 97.08 | 97.58 | 97.58 |
| TOTAL % | 100.00 | 100.00 | 100.00 |

Table 6 sets forth the results of an experiment using the formulations shown in Table 5 on American Cockroaches.

TABLE 6

| Observed vs. Expected Results | Formulations | Trisiloxane Surfactants | Avg. 30 second KD % control |
|---|---|---|---|
| Observed Result | I | 0.5% Silwet L-77 | 40% |
| Observed Result | H | 0.5% Silwet REACH | 50% |
| Observed Result | G | 0.5% Silwet L-77 + 0.5% Silwet REACH blend | 95% |
| Expected Result | | 0.5% Silwet L-77 + 0.5% Silwet REACH blend | 70%* |

*Colby equation calculation

Using S. R. Colby's equation, an Expected Result (knockdown) was calculated and then compared to the Observed Results achieved when the formulations containing the Silwet L-77/Silwet REACH blend and the individual trisiloxane surfactants were employed. The Observed Result achieved utilizing the blend was 25% greater than the Expected Result which clearly demonstrates the significant and unexpected synergy achieved between Silwet REACH and Silwet L-77 in the blend formulation, whereas the uncombined individual trisiloxane surfactants demonstrated poor knockdown activity:

EXAMPLE 4

In Table 7 below, compositions of the formulations, as prepared in Example 1 above, include the indicated trisiloxane-surfactant blends at an equal total concentration of 1.0%, but combined at various ratios as shown in Table 7, with no other active ingredient incorporated into the composition. Components are presented in weight percent.

TABLE 7

| | Formulations | | |
|---|---|---|---|
| Components | J | K | L |
| Silwet 408 (Silwet REACH) | 0.75 | 0.5 | 0.25 |
| Silwet L-77 | 0.25 | 0.5 | 0.75 |
| Water, Purified | 99.0 | 99.0 | 99.0 |
| Total % | 100.0 | 100.0 | 100.0 |

The following table presents the results of an experiment using the formulations presented in Table 7, prepared as noted above, applied to American cockroaches.

TABLE 8

| Trisiloxane Surfactant Blends | Formulation | Ratio | Knockdown of American Cockroach Within 60 Seconds After Treatment |
|---|---|---|---|
| Silwet REACH/Silwet L-77 | J | 75:25 | 100% |
| Silwet REACH/Silwet L-77 | K | 50:50 | 100% |
| Silwet REACH/Silwet L-77 | L | 25:75 | 100% |

As shown by the results in Table 8, the knockdown effect through the use of the blend of Silwet REACH and Silwet L-77 is very effective at multiple ratios depicted in this Example 4 as ranging from 75:25 to 50:50 to 25:75 (3:1, 1:1, 1:3).

EXAMPLE 5

In Table 9 below, compositions of the formulations as prepared in Example 1 above, include Silwet REACH/Silwet L-77 blends at a range of concentrations from 0.05% to 1.5% with no other active ingredients in the compositions. Components are presented in weight percent.

TABLE 9

| | Formulations | | | | |
|---|---|---|---|---|---|
| Components | M | N | O | P | Q |
| Silwet 408 (Silwet REACH) | 0.025 | 0.05 | 0.25 | 0.5 | 0.75 |
| Silwet L-77 | 0.025 | 0.05 | 0.25 | 0.5 | 0.75 |
| Water, Purified | 99.95 | 99.9 | 99.5 | 99.0 | 98.5 |
| Total, % | 100.0 | 100.0 | 100.0 | 100.0 | 100.0 |

The following table presents the results of an experiment using the formulations described in Table 9, prepared as noted above, applied American cockroaches.

TABLE 10

| Trisiloxane Surfactant Blends | Formulation | Knockdown of American Cockroach Within 60 Seconds After Treatment |
|---|---|---|
| Silwet L-77/Silwet REACH | M | 32% |
| Silwet L-77/Silwet REACH | N | 100% |
| Silwet L-77/Silwet REACH | O | 100% |
| Silwet L-77/Silwet REACH | P | 100% |
| Silwet L-77/Silwet REACH | Q | 100% |

The results in Table 10 indicate that there is a minimum effective concentration at which the Silwet L-77/Silwet REACH blend provides the desired knockdown of American cockroaches. That is, it was shown that the blend performs poorly at a concentration of 0.05%, whereas, at 0.1% and above, the knockdown (KD) effect of the blend is excellent.

EXAMPLE 6

In Table 11 below, the compositions of the formulations, as prepared in Example 1 above, include the indicated trisiloxane surfactant or surfactants with no active pesticidal ingredient added to the formulation. Components are presented in weight percent.

TABLE 11

| | Formulations | | |
|---|---|---|---|
| Components | R | S | T |
| Silwet 408 (Silwet REACH) | 0.5 | 0.5 | — |
| Silwet L-77 | 0.5 | — | 0.5 |
| Water, Purified | 99.0 | 99.5 | 99.5 |
| Total % | 100.0 | 100.0 | 100.0 |

The following table presents the results of an experiment where the formulations, having the concentration of components shown above in Table 11, were evaluated for knockdown of American cockroaches. The trisiloxane surfactant blend of Silwet REACH/Silwet L-77 was compared with each of the individual trisiloxane surfactants. S. R. Colby's Synergy Equation was used to determine if the combination of Silwet REACH and Silwet L-77 provided an unexpected synergistic response in knockdown (KD) of American cockroaches as compared with each of the trisiloxane surfactants separately.

TABLE 12

| Observed vs. Expected Results | Formulations | Trisiloxane Surfactants | Knockdown of American Cockroaches (seconds after treatment) | | |
|---|---|---|---|---|---|
| | | | 32 | 33 | 34 |
| Observed Result | R | 0.5% Silwet L-77 | 54.6% | 64.0% | 72.6% |
| Observed Result | S | 0.5% Silwet REACH | 29.9% | 32.5% | 35.2% |
| Observed Result | T | 0.5% Silwet L-77 + 0.5% Silwet REACH Blend | 81.4% | 87.6% | 92.2% |
| Expected Result | | 0.5% Silwet L-77 + 0.5% Silwet REACH Blend | 68.2%* | 75.7%* | 82.3%* |

*Colby equation calculation

Using S. R. Colby's equation, an Expected Result (% knockdown) was calculated and then compared to the Observed Result when the formulations containing the Silwet L-77+Silwet REACH blend and each of the individual trisiloxane surfactants were tested on American cockroaches. The Observed Results employing the Silwet REACH+Silwet L-77 blends, at each of the intervals after treatment as shown in Table 12, were higher than the corresponding Expected Result, These Observed Results clearly demonstrate the significant and unexpected synergy achieved with Silwet L-77 and Silwet REACH blends. To the contrary, the uncombined individual trisiloxane surfactants demonstrate fair to poor knockdown activity which do not exceed the Expected Result at each of the intervals after treatment as calculated using the Colby equation.

EXAMPLE 7

In Table 13 below, the compositions of the formulations, as prepared in Example 1 above, include the indicated trisiloxane surfactant with and without an active pesticidal ingredient added to the formulation. Components are presented in weight percent.

TABLE 13

| | Formulations | |
|---|---|---|
| Components | U | V |
| Talstar MUP (13% bifenthrin) | 0.39 | — |
| Silwet 408 (Silwet REACH) | 0.5 | 0.5 |
| Silwet L-77 | 0.5 | 0.5 |
| Other inert ingredients | 1.53 | — |
| Water, Purified | 97.08 | 99.0 |
| Total % | 100.0% | 100.0 |

The following table presents the results of an experiment using the formulations specified in Table 13, prepared as noted above, applied to house crickets (*Acheta domesticus*).

TABLE 14

| Trisiloxane Surfactant | Formulation | Knockdown of House Crickets within 30 and 60 seconds after Treatment | |
|---|---|---|---|
| | | 30 | 60 |
| Silwet L-77/Silwet REACH Blend (with bifenthrin) | U | 92% | 100% |

TABLE 14-continued

| Trisiloxane Surfactant | Formulation | Knockdown of House Crickets within 30 and 60 seconds after Treatment | |
|---|---|---|---|
| | | 30 | 60 |
| Silwet L-77/Silwet REACH Blend (without bifenthrin) | V | 96% | 100% |

As shown in the results summarized in Table 14, the blend of trisiloxane surfactants, Silwet L-77 and Silwet REACH, whether combined with an active ingredient OF not, provided the desired knockdown (KD) effect on house crickets within 60 seconds after treatment.

Although the invention has been described in its preferred forms with a certain degree of particularity, it is to be understood that the present disclosure has been made by way of example only. Numerous changes in the details of the compositions and ingredients therein as well as the methods of preparation and use will be apparent without departing from the spirit and scope of the invention, as defined in the appended claims.

What is claimed is:

1. A composition comprising a blend of a first silicone surfactant of the formula

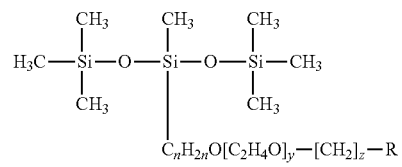

wherein n=2-4, y=3-10, z=0-5, and R=alkyl having 1-4 carbon atoms, and a second silicone surfactant of the formula

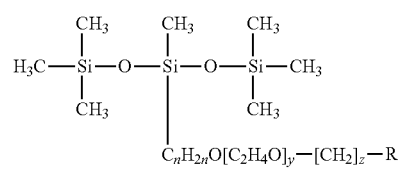

wherein n=2-4, y=3-10, z=0-5, and R=OH, H, O-alkyl having 1-4 carbon atoms, provided that when z=0, R=H and when z=1-5, R=OH or O-alkyl having 1-4 carbon atoms, wherein the composition is a liquid solution of the first and second silicon surfactants and the total weight percent of the first silicone surfactant and the second silicone surfactant ranges from about 0.1% to about 1.5% by weight;

wherein the first surfactant and the second surfactant are present in a concentration such that the composition exhibits synergistic knockdown (KD) level on treated arthropods in a period of less than about 60 seconds after treatment of the arthropods with the composition.

2. The composition of claim 1, wherein the ratio of first silicone surfactant to second silicone surfactant ranges from 1:3 to 3:1.

3. The composition of claim 1, wherein the first silicone surfactant is present in the composition at a concentration of at least 0.05% by weight and the second silicone surfactant is present in the composition at a concentration of at least 0.05% by weight.

4. The composition of claim 1, comprising at least 50% by weight water.

5. The composition of claim 4, comprising at least 97.08% by weight water.

6. The composition of claim 1, wherein the composition is free of any agriculturally active ingredient.

7. The composition of claim 1, wherein the composition comprises an amount of agriculturally active ingredient.

8. The composition of claim 1, wherein the amount of agriculturally active ingredient in the composition ranges from about 0.001 to about 5% by weight.

9. The composition of claim 8, wherein the amount of agriculturally active ingredient in the composition ranges from about 0.03 to about 0.5% by weight.

10. The composition of claim 9, wherein the amount of agriculturally active ingredient in the composition ranges from about 0.05 to about 0.25% by weight.

11. The composition of claim 1, wherein the first silicone surfactant is of the formula

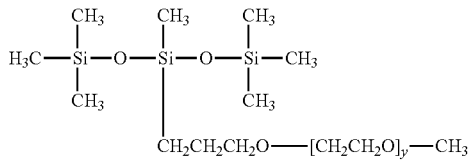

wherein y=6-10.

12. The composition of claim 1, wherein the first silicone surfactant is of the formula

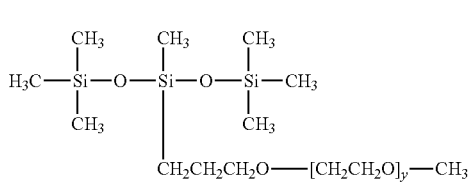

wherein y=8.

13. The composition of claim 1, wherein the second silicone surfactant is of the formula

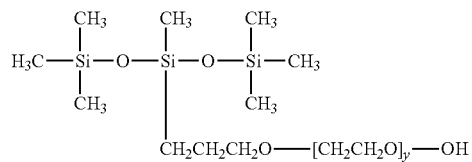

wherein y=6-10.

14. The composition of claim 1, wherein the second silicone surfactant is of the formula

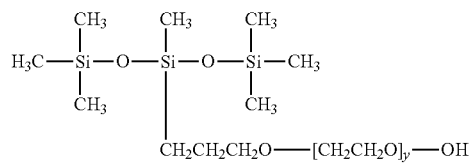

wherein y=8.

15. The composition of claim 1, wherein the first silicone surfactant is of the formula

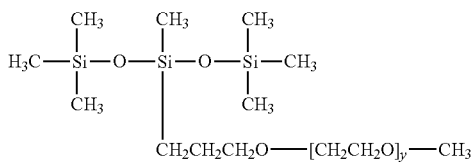

wherein y=6-10 and the second silicone surfactant is of the formula

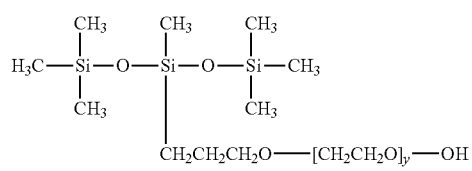

wherein y=6-10.

16. The composition of claim 1, wherein the first silicone surfactant is of the formula

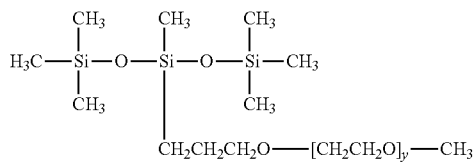

wherein y=8
and the second silicone surfactant is of the formula

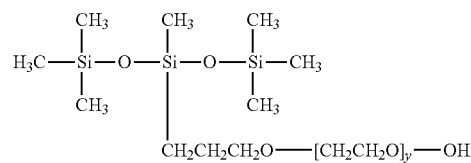

wherein y=8.

17. The composition of claim 1, wherein the first surfactant and the second surfactant are present in a concentration such that the composition exhibits synergistic knockdown (KD) level on treated arthropods in a period of less than about 60 seconds after treatment of the arthropods with the composition.

18. The composition of claim 1, wherein the synergistic knockdown (KD) level on treated arthropods is at a rate of at least about 80% within the period of less than about 60 seconds after treatment of the arthropods with the composition.

19. The composition of claim 1, wherein the second silicone surfactant is of the formula

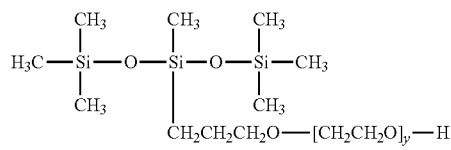

wherein y=6-10.

20. The composition of claim 1, wherein the second silicone surfactant is of the formula

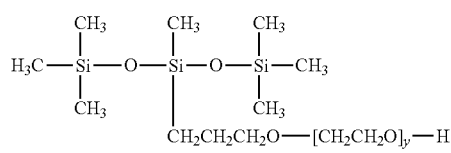

wherein y=8.

21. The composition of claim 1, wherein the first silicone surfactant is of the formula

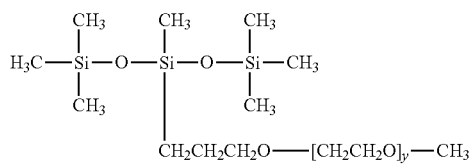

wherein y=6-10
and the second silicone surfactant is of the formula

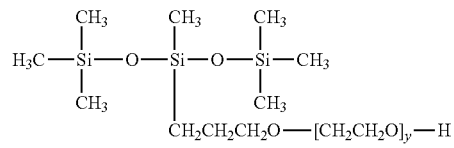

wherein y=6-10.

22. The composition of claim 1, wherein the first silicone surfactant is of the formula

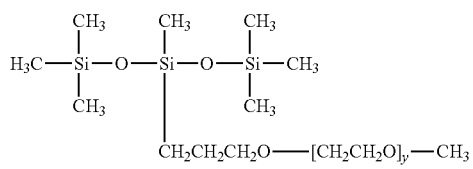

wherein y=8
and the second silicone surfactant is of the formula

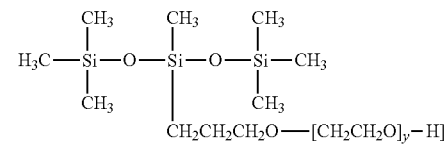

wherein y=8.

* * * * *